United States Patent
Corbin et al.

(10) Patent No.: US 10,617,449 B2
(45) Date of Patent: Apr. 14, 2020

(54) TAP MARKER

(71) Applicant: Stryker European Holdings I, LLC, Kalamazoo, MI (US)

(72) Inventors: Erika Corbin, Mahwah, NJ (US); Nicole Renee Favetta, Haverstraw, NY (US); Steven Krause, Oakland, NJ (US); Abram Reitblat, Monroe, NY (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 118 days.

(21) Appl. No.: 15/399,837

(22) Filed: Jan. 6, 2017

(65) Prior Publication Data

US 2017/0196597 A1 Jul. 13, 2017

Related U.S. Application Data

(60) Provisional application No. 62/276,456, filed on Jan. 8, 2016.

(51) Int. Cl.
*A61B 17/60* (2006.01)
*A61B 17/70* (2006.01)
*A61B 17/02* (2006.01)

(52) U.S. Cl.
CPC ........ *A61B 17/7049* (2013.01); *A61B 17/025* (2013.01); *A61B 17/7077* (2013.01); *A61B 17/7082* (2013.01); *A61B 17/7032* (2013.01); *A61B 2017/0256* (2013.01)

(58) Field of Classification Search
CPC combination set(s) only.
See application file for complete search history.

(56) References Cited

U.S. PATENT DOCUMENTS

| | | | |
|---|---|---|---|
| 5,928,139 A * | 7/1999 | Koros | A61B 17/0206 600/205 |
| 6,090,113 A | 7/2000 | Le Couedic et al. | |
| 6,648,891 B2 * | 11/2003 | Kim | A61B 17/0206 606/102 |
| 6,858,030 B2 | 2/2005 | Martin et al. | |
| 7,156,874 B2 | 1/2007 | Paponneau et al. | |
| 7,637,950 B2 | 12/2009 | Baccelli et al. | |
| 7,985,256 B2 | 7/2011 | Grotz et al. | |
| 8,157,809 B2 | 4/2012 | Butters et al. | |
| 8,216,317 B2 | 7/2012 | Thibodeau | |
| 2003/0055430 A1 * | 3/2003 | Kim | A61B 17/0206 606/331 |
| 2005/0021040 A1 * | 1/2005 | Bertagnoli | A61B 17/025 606/90 |
| 2005/0203533 A1 * | 9/2005 | Ferguson | A61B 17/025 606/90 |
| 2006/0235422 A1 * | 10/2006 | Keller | A61B 17/025 606/90 |

(Continued)

*Primary Examiner* — Jan Christopher L Merene
(74) *Attorney, Agent, or Firm* — Lerner, David, Littenberg, Krumholz & Mentlik, LLP (57) ABSTRACT

Methods and apparatus for compressing and/or distracting bones are described herein. In one such method, a tap marker is engaged with a bone and a compressor/distractor device. The tap marker can be removed after moving the bone and a bone screw can be inserted into the space previously occupied by the tap marker. A rod or other fixation element can then be attached to the bone screw.

19 Claims, 11 Drawing Sheets

(56) References Cited

U.S. PATENT DOCUMENTS

| | | | | |
|---|---|---|---|---|
| 2006/0241769 A1* | 10/2006 | Gordon | ............. | A61B 17/7005 |
| | | | | 623/17.13 |
| 2010/0331849 A1* | 12/2010 | Riesinger | ........... | A61B 17/7077 |
| | | | | 606/90 |
| 2013/0310942 A1* | 11/2013 | Abdou | .................. | A61F 2/4455 |
| | | | | 623/17.16 |
| 2014/0012269 A1* | 1/2014 | Bass | .................... | A61B 17/025 |
| | | | | 606/90 |
| 2015/0066042 A1* | 3/2015 | Cummins | .......... | A61B 17/7037 |
| | | | | 606/104 |
| 2016/0106408 A1 | 4/2016 | Ponmudi et al. | | |

* cited by examiner

TAP MARKER

CROSS-REFERENCE TO RELATED APPLICATIONS

This application claims the benefit of the filing date of U.S. Provisional Patent Application No. 62/276,456 filed Jan. 8, 2016, the disclosure of which is hereby incorporated herein by reference.

BACKGROUND OF THE INVENTION

The present invention relates to a method of positioning bone. Specifically, a method of positioning vertebrae using a tap marker is described herein.

Current methods of distracting or compressing vertebrae include screw based decompression. One advantage of using screws during decompression is they provide a landmark to track the location of bone during the procedure. The screws used for decompression typically include polyaxial screws, which include a bone screw and head (tulip) that can be moved with respect to the screw. These polyaxial screws may be pre-assembled or may be modular in design. Polyaxial bone screws are widely utilized as they allow for greater flexibility is use and take less space in the surgical site.

However, there are also disadvantages associated with using bone screws for distraction or compression. For instance, forces are put on the screws during distraction which can possibly cause damage to the screw/tulip interface. Elongation of bone from over-distraction (windshield wiper effect) when using screws can also occur, which may require the screw to be replaced with a larger screw. Bone screws also frequently disengage from the distractor under a compressive load. This forces the surgeon to skip the distraction step or use an additional instrument such as a lamina spreader. Therefore, a need exists for an improved method of positioning bone.

BRIEF SUMMARY OF THE INVENTION

One aspect of the disclosure includes a method for moving a vertebral body which desirably includes inserting a first member into a first vertebral body at a first location, moving the first member to move the first vertebral body, removing the first member from the first vertebral body, and positioning a first anchor into the first vertebral body at the first location. The method may include creating an opening in the vertebra prior to the inserting step and the inserting step may include inserting the first member in the opening.

The first member can be a tap and the inserting step may include creating a threaded opening at the first location. The first anchor may be a bone screw or a pedicle screw with a head adapted to receive a rod and the method can further include coupling a rod to the screw head. The first location may be at a pedicle of the first vertebral body. The method may further comprise inserting a second member into a second vertebral body and moving the second vertebral body with respect to the first vertebral body. The moving step can include engaging an instrument with the first and second members to permit at least one of compression and distraction of the first and second vertebral bodies. The creating an opening step can include drilling a hole in the vertebral body. The method can further include inserting an implant between the first and second vertebral bodies.

Another aspect of the disclosure describes a method of moving vertebral bodies comprising inserting a first tap in a first vertebral body to create a first threaded opening in the first vertebral body; inserting a second tap in a second vertebral body to create a second threaded opening in the second vertebral body; coupling an instrument to the taps while the taps are within the first and second threaded openings; moving the first and second vertebral bodies with the instrument; removing the first and second taps; inserting a first bone screw in the first threaded opening; and inserting a second bone screw in the second threaded opening.

The first tap may have a tap head and the first bone screw can have a screw head wherein the tap head is smaller than the screw head. The moving step may comprise at least one of compression and distraction of the vertebral bodies. The first member can include a head separated from a threaded section by an extension and the moving step can include engaging the extension with an instrument.

Another aspect of the disclosure describes a method of compressing or distracting bone which includes inserting first and second taps into first and second bones to create first and second threaded openings; coupling an instrument to the first and second taps; moving the first and second bones with the instrument while the taps are in the first and second threaded openings; removing the taps; inserting first and second bone screws into the first and second threaded openings; and coupling a rod to the first and second bone screws. The first and second bones can be first and second vertebral bodies.

DETAILED DESCRIPTION

Figure 1:
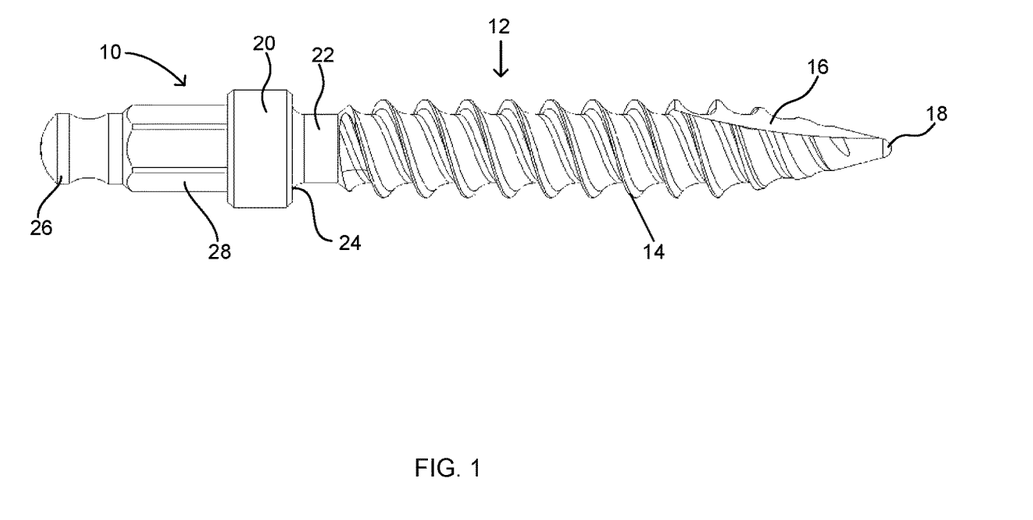
FIG. 1 illustrates a tap marker in accordance with one embodiment of the present invention.

FIG. 1 illustrates one embodiment of a tap marker 10 in accordance with the present disclosure. Tap marker 10 shown in FIG. 1 includes a body 12 having a helical thread 14. Tap marker 10 includes a cutting flute 16 extending from a tip 18 along body 12. Cutting flute 16 allows tap marker 10 to self-drill into the bone. Of course, the tap marker could also be formed without a flute and inserted into a pre-drilled hole. Although shown as a solid structure, it is contemplated to form tap marker 10 as a cannulated component, thus allowing for its placement over a K-wire or the like.

A neck 22 is formed on body 12 adjacent thread 14. As will be explained in greater detail below, a distraction instrument or other component can be coupled to an extension 28 or another portion (e.g., neck 22) to move tap marker 10. A radius 24 forms the transition between neck 22 and a collar 20. Radius 24 reduces stress concentration along the tap marker during insertion or movement of the tap marker. Collar 20 prevents axial translation of the distraction tool during a surgical procedure when the instrument engages the tap marker at neck 22. The collar also prevents over-insertion of the tap marker into the bone, as well as cooperation with a tap marker adapter (discussed below). Tap marker 10 includes an extension 28 positioned between collar 20 and head 26 that is adapted to engage an insertion instrument. Extension 28 shown has a cross-sectional shape adapted to engage an insertion instrument (e.g. hexagon, square, ovular, octagonal, etc . . . ). Of course, head 26 could also be adapted to engage a driving instrument. For instance, head 26 could exhibit a shape similar to that of extension 28. In other embodiments, head 26 could be designed with a female engagement member (e.g. Phillips, Torx, socket).

Figure 2:
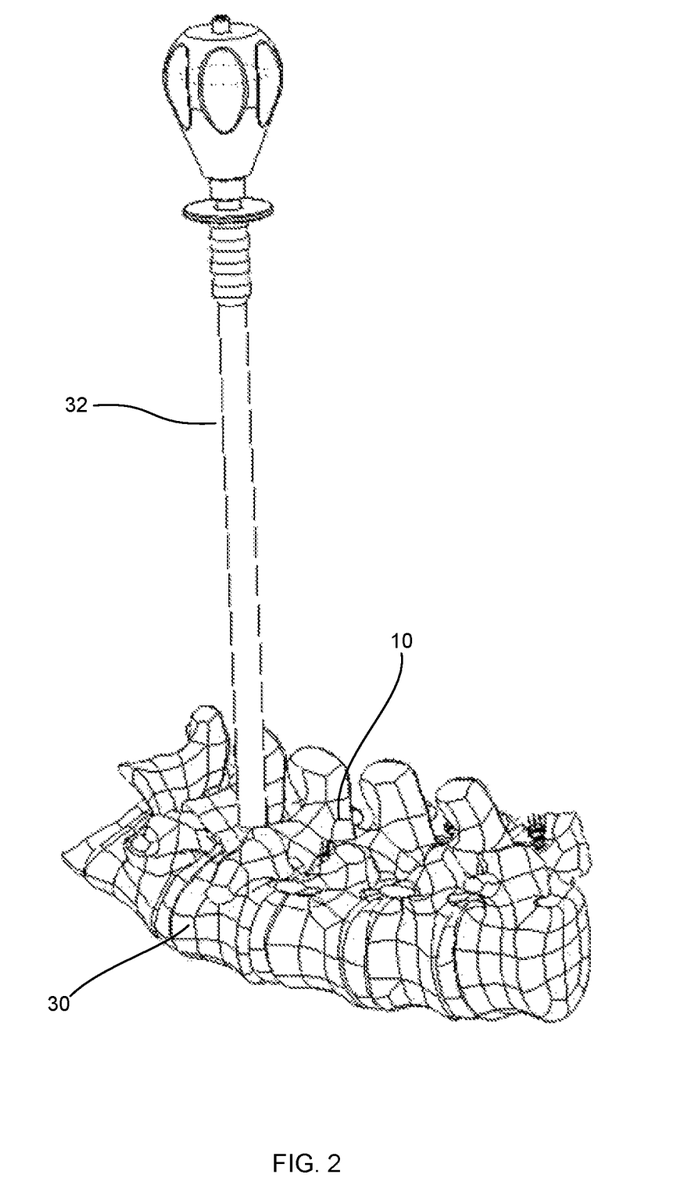
FIG. 2 illustrates an insertion instrument coupled to the tap marker of FIG. 1.
Figure 3A:
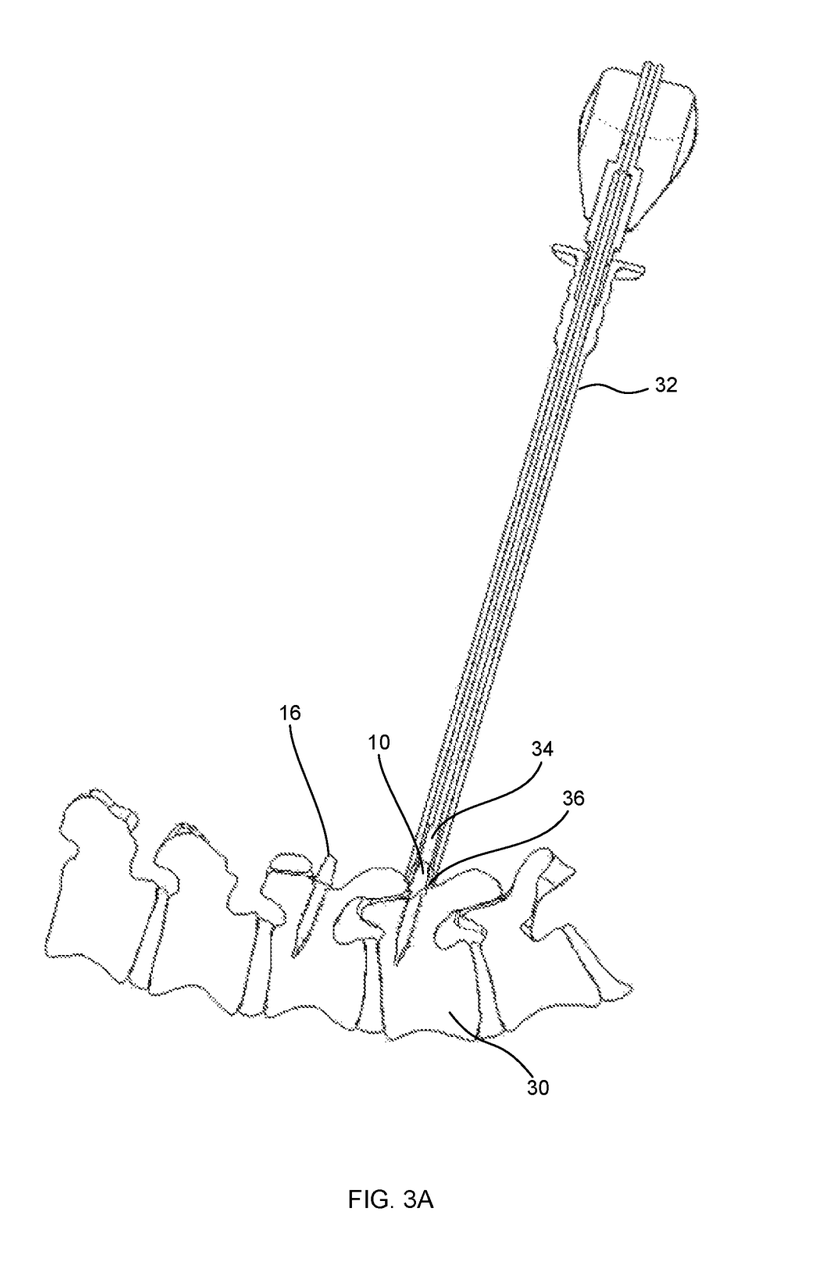
FIG. 3A is a cross-sectional view detailing the coupling of the insertion instrument and tap marker of FIG. 2.
Figure 3B:
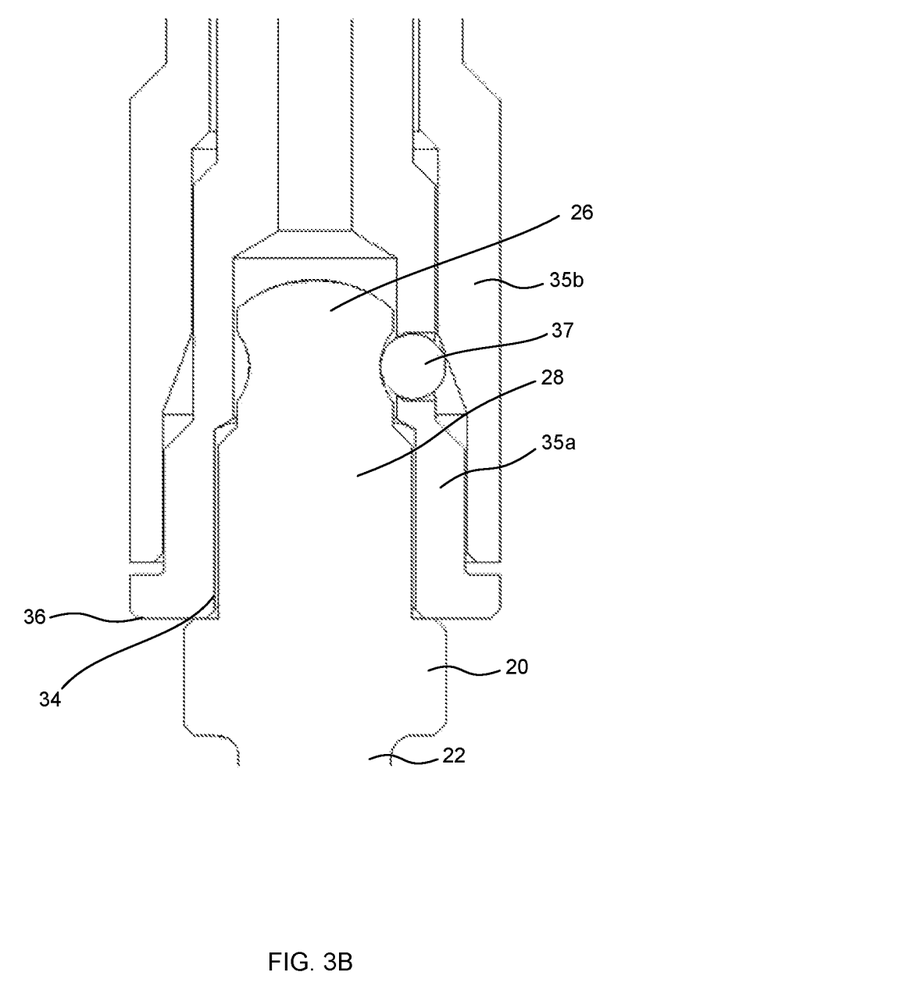
FIG. 3B is a cross-sectional view focusing on the coupling of the insertion instrument and tap marker.

FIGS. 2-3B illustrate an insertion instrument 32 coupled to the tap marker 10. The insertion instrument has an opening 34 at its distal end 36 adapted to receive head 26 and extension 28 of tap marker 10. The insertion instrument preferably exhibits a shape complimentary to the shape of extension 28, but of course, could also have any desired engagement feature (e.g. Phillips, Torx, socket) to engage tap marker 10. Likewise, in concert with the foregoing, opening 34 could be designed to solely receive head 26, or insertion instrument 32 may include a male engagement member for engaging a female engagement member in head 26. In the particular arrangement best depicted in FIG. 3B, opening 34 is designed to receive both head 26 and extension 28 and instrument 32 further includes inner and outer members 35a and 35b and detent 37. The operation of these components is such that movement of the inner and outer members with respect to each other results in detent being moved and/or fixed into a position in which head 26 is captured. This allows for marker 10 to be retained by instrument 32, which allows for easy manipulation of the marker during surgery. The insertion instrument of FIGS. 2-3 is manually operated but could also be a powered driver (e.g. screw gun). In other embodiments, insertion instrument 32 may be designed a torque-limiting instrument, a ratchet instrument or the like. To facilitate acceptance of a K-wire extending through tap marker 10, portions or the entirety of instrument 32 may be cannulated.

Figure 4A:
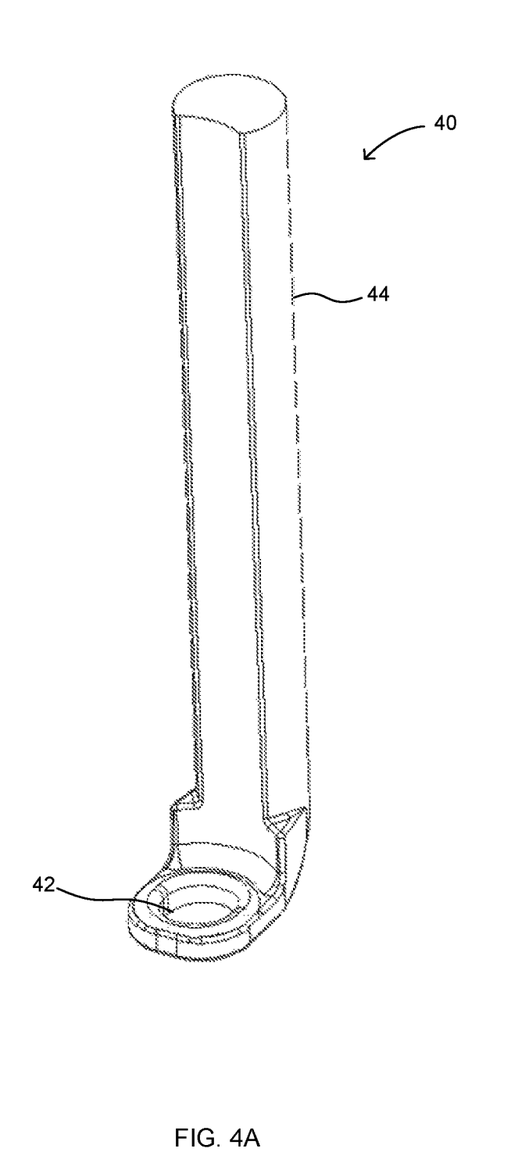
FIGS. 4A and 4B illustrate tap marker adapters in accordance with embodiments of the present invention.
Figure 4B:
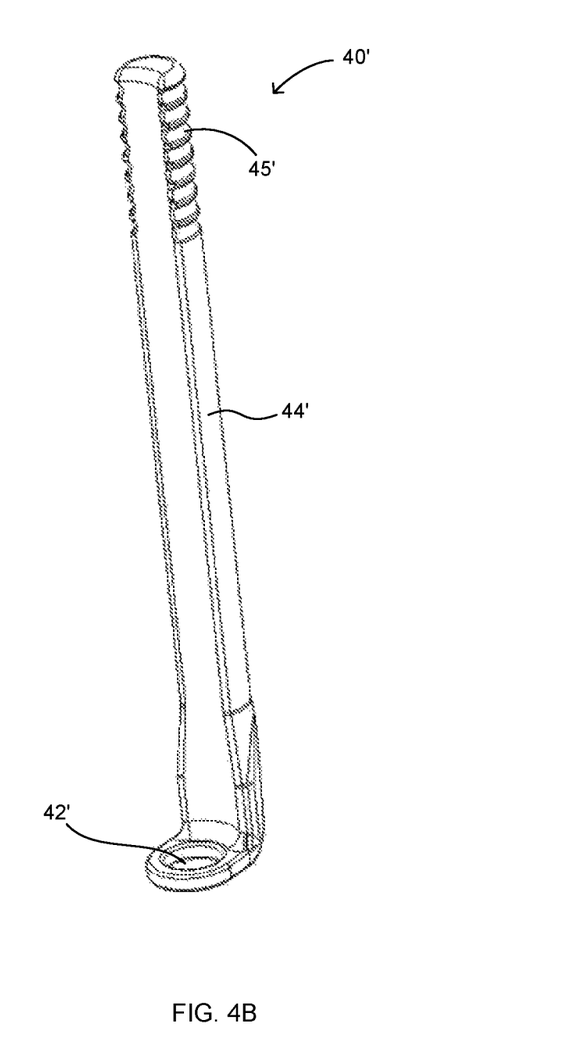

FIG. 4A illustrates a tap marker adapter 40. As shown, the adapter includes an aperture 42 and a shaft 44, which in the embodiment shown are offset with respect to one another. It is contemplated though to have the two elements aligned in different fashions, including coaxially (e.g., shaft 44 would in effect be partially or fully cannulated). Aperture 42 is shown as exhibiting a size designed to accept body 12 of tap marker 10, while abutting up against collar 20. Of course, other sizes are contemplated for accepting different portions of tap marker 10. Shaft 44 is shown as exhibiting a smooth semi-circular outer-surface, but other embodiments may be of any shape and/or may include surface roughening or the like. For instance, FIG. 4B illustrates another embodiment tap marker adapter 40', which includes a shaft 44' that includes roughened surface 45'. Preferably, shafts 44 and 44' are designed to be accepted by portions of the distraction instrument discussed below, where roughened surface 45' may further aid in keeping the adapter coupled with the distraction instrument.

Figure 5:
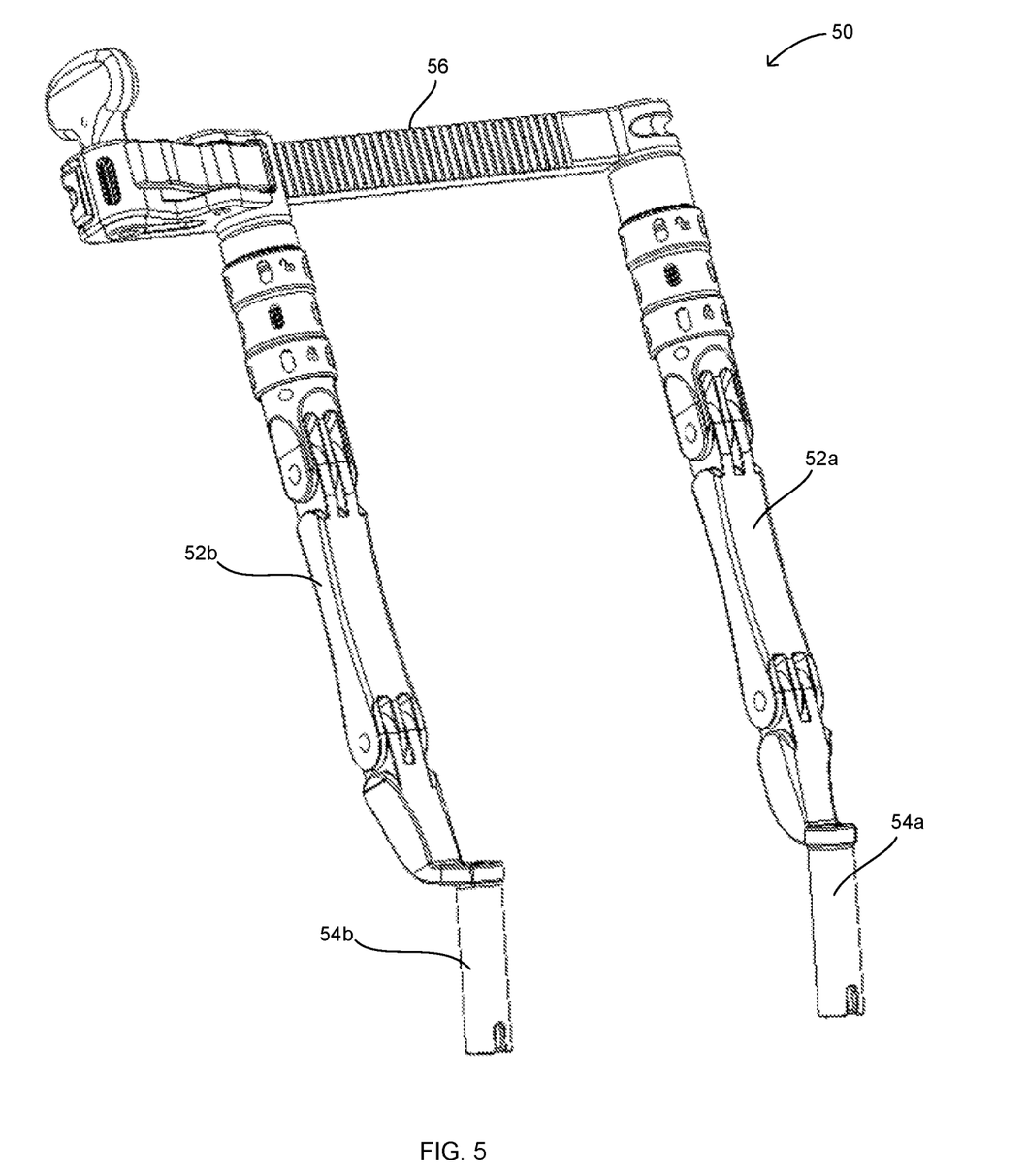
FIG. 5 illustrates a distraction instrument in accordance with one embodiment of the present invention.

Although many different distraction instruments may be employed in connection with the present invention, FIG. 5 depicts one such instrument 50. As shown, distraction instrument 50 includes two arms 52a and 52b with barrels 54a and 54b, respectively, on their distal ends and coupled with a distraction element 56 on their proximal ends. Arms 52a and 52b are shown as being jointed, which allows manipulation of construct to facilitate use in different surgical settings. However, it is contemplated that the arms may be of a solid construction or articulatable in different areas, such as at the coupling with distraction element 56. Barrels 54a and 54b are shown fixed to arms 52a and 52b, but could also be capable of moving with respect to the arms. The barrels exhibit a semi-circular shape for cooperation with the above-discussed shafts 44, but, like those latter elements, can be of any shape. The semi-circular design does allow for a rotationally fixed arrangement between the barrels and the shafts which is beneficial in the intended use of the instrument. Distraction element 56 is a rack and pinion design, but of course could be many different known arrangements suitable for distracting or compressing vertebrae. For instance, while the design of distraction instrument 50 is similar to known Caspar distracters, a plier-like design or the like could be employed. Other suitable distraction instruments contemplated for use with the present system are described in U.S. Pat. Nos. 6,090,113 and 8,157,809, the disclosures of which are hereby incorporated by reference herein.

In use, tap markers 10 are first inserted into vertebral bodies 30. Prior to the insertion of the markers, the necessary incisions are made to establish the necessary corridors for the procedure. These incisions may be of any size depending upon the type of procedure being conducted or the number of levels of spine being fused. For instance, the present invention can be utilized in more traditional procedures, which require larger incisions or percutaneous MIS procedures, which require smaller incisions. After the incisions are performed the vertebral bodies are prepared for acceptance of tap markers 10. This may include imagining to determine a proper insertion orientation, pre-drilling to create an initial corridor for the markers and/or inserting a K-wire or the like to aid in the placement of the markers. Use of K-wires, as discussed above, generally requires tap markers 10 to be cannulated. In the case of pre-drilled holes, such may be longer or shorter than body 12 of tap marker 10.

Once the vertebral bodies are at least initially prepared, tap markers 10 are inserted at the desired location via insertion instrument 32 (as shown in FIGS. 2-3B). The tap markers may also be placed in different orientations, such as for traditional pedicle screw placement or for a mid-line approach. The leading edge of flute 16 bores a hole (or a larger hole in the case where pre-drilled holes are made) in the bone as tap marker 10 is inserted at the desired location, for instance, into a pedicle of a vertebral body. Thus, threads 14 create a threaded hole as tap marker 10 is advanced into the vertebral body. In certain embodiments, body 12 of tap marker 10 is first placed through aperture 42 of tap marker adapter 40. This results in collar 20 abutting up against adapter 40, which is adjacent the vertebra 30. However, a user could elect to stop inserting the tap marker prior to the collar pinning adapter against vertebral body 30. The particular design of tap marker 10 and adapter 40 is such that shaft 44 can be situated in different orientations upon rotation of the adapter about the marker. Other designs are contemplated where only a single orientation is allowed.

Once inserted, the tap marker and adapter construct occupies less volume in the surgical space exterior of vertebral body 30 than would be occupied by screws having a tulip head, which reduces interference between the head and the vertebral body or other heads. The construct is also preferably stronger and more fixed than such screws would exhibit. Thus, the clinician has greater freedom to maneuver the vertebral bodies into their desired orientation. Although the bone illustrated is a vertebral body, the system could be used on any bone or, in the case of fractures, bone fragments.

Figure 6:
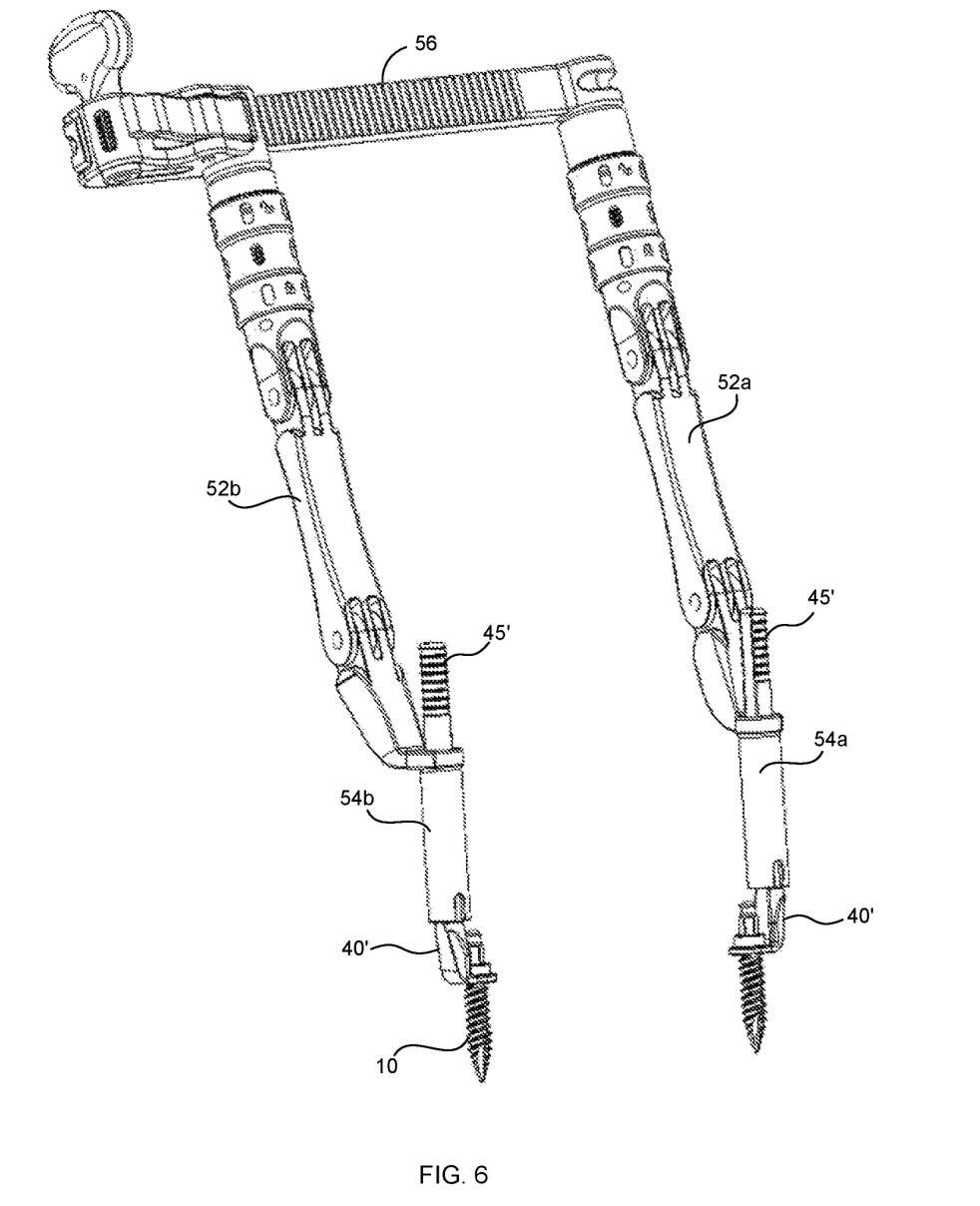
FIG. 6 illustrates the distraction instrument of FIG. 5 coupled to two tap marker adapters of FIG. 4 engaged with two tap markers of FIG. 1.

With multiple tap markers 10 and tap marker adapters 40' in place, barrels 54*a* and 54*b* can be placed over shafts 44'. This is shown in FIG. 6, albeit without the adapters and markers having been engaged with vertebral bodies. Preferably, barrels 54*a* and 54*b* are designed to freely slide over shafts 44', but other designs are contemplated. For instance, shafts 44 could be designed to positively engage barrels 54*a* and 54*b*, thereby forming a fixed construct. This could be achieved by employing shafts that have a ball detent or other collapsible structure that, after placement in the barrels, expands to create a fixed construct. In any event, this marker, adapter and distraction instrument construct allows a single instrument to be used to compress or distract the vertebral bodies as desired. Although the foregoing discussion is specific to adapter 40', above-discussed adapter 40 could likewise be utilized. As shown, roughened surfaces 45' of adapters 40' aid in creating a firmer connection between barrels 54*a* and 54*b* and shafts 44'.

After the vertebral bodies are moved, the surgeon may perform several different steps depending upon the procedure being performed. For instance, it is envisioned that, at this time, a fusion implant can be inserted between adjacent vertebral bodies. In this regard, any type of such implant may be utilized and many different types of insertions methods may be utilized. Implants of the PLIF, TLIF and lateral types can be inserted in any known fashion, with and without additional bone promoting substances. For instance, implants like those disclosed in U.S. Pat. Nos. 7,156,874; 7,637,950; 7,985,256; and 8,216,317, the disclosures of which are hereby incorporated by reference herein can be utilized. Of course, it should also be appreciated that the implants could be inserted both before and after removal of distraction instrument 50, as well as after removal of tap markers 10.

When so desired, the tap markers are removed from the vertebral bodies 30. Traditional pedicles screws can then be positioned in the threaded bone holes created by the tap markers. An example of such a pedicle screw is disclosed in U.S. Pat. No. 6,858,030, the disclosure of which is hereby incorporated by reference herein. A rod can then be secured to the screws, as in well-known pedicle screw procedures.

In certain embodiments of the present invention, the tap markers may be longer or shorter than the pedicle screws that are ultimately placed. Likewise, the size of body 12 or the threads thereon can be of any relationship to similar elements on the pedicle screws. For instance, in one embodiment, body 12 may have a core that is smaller than a similar core of the pedicle screw, but its threads can be wider than the threads of the pedicle screw. The threads of the various elements of the present invention may of course be of any shape, size, profile, pitch, angle, orientation, etc. . . . . . Likewise, it is contemplated to size taps such that they are either longer or shorter than the pedicle screws that are ultimately implanted.

Multiple tap markers 10, adapters 40 (and/or adapters 40'), K-wires, pedicle screws, distraction instruments and the like may be provided in a kits allowing for an entire surgical procedure to be conducted. These components may be provided in a container or multiple containers for easy transport and/or sterilization. As mentioned above, the present invention allows for the ultimate placement of pedicle screws and rods, and can be performed on any number of levels of the spine. For instance, as little as two vertebral bodies may be fused together utilizing the apparatus and methods of the present invention, but more than two is clearly within the purview of the present invention. While standard pedicle screws and rods are discussed above, it is contemplated to utilize biased angle screws, growing rods and flexible or dynamic rods in connection with the present invention.

The tools utilized may also vary depending upon the particular approach/methodology employed. For instance, insertion instrument 32 may be designed to only insert tap markers 10, but could, in some embodiments, also be utilized to insert the pedicle screws ultimately placed. Similarly, the use of adapters 40 and 40' are discussed above. It is envisioned that distractions instruments could be engaged directly with the tap markers themselves. For instance, barrels 54*a* and 54*b* could be sized and shaped to receive extensions 28 of markers 10.

Figure 7:
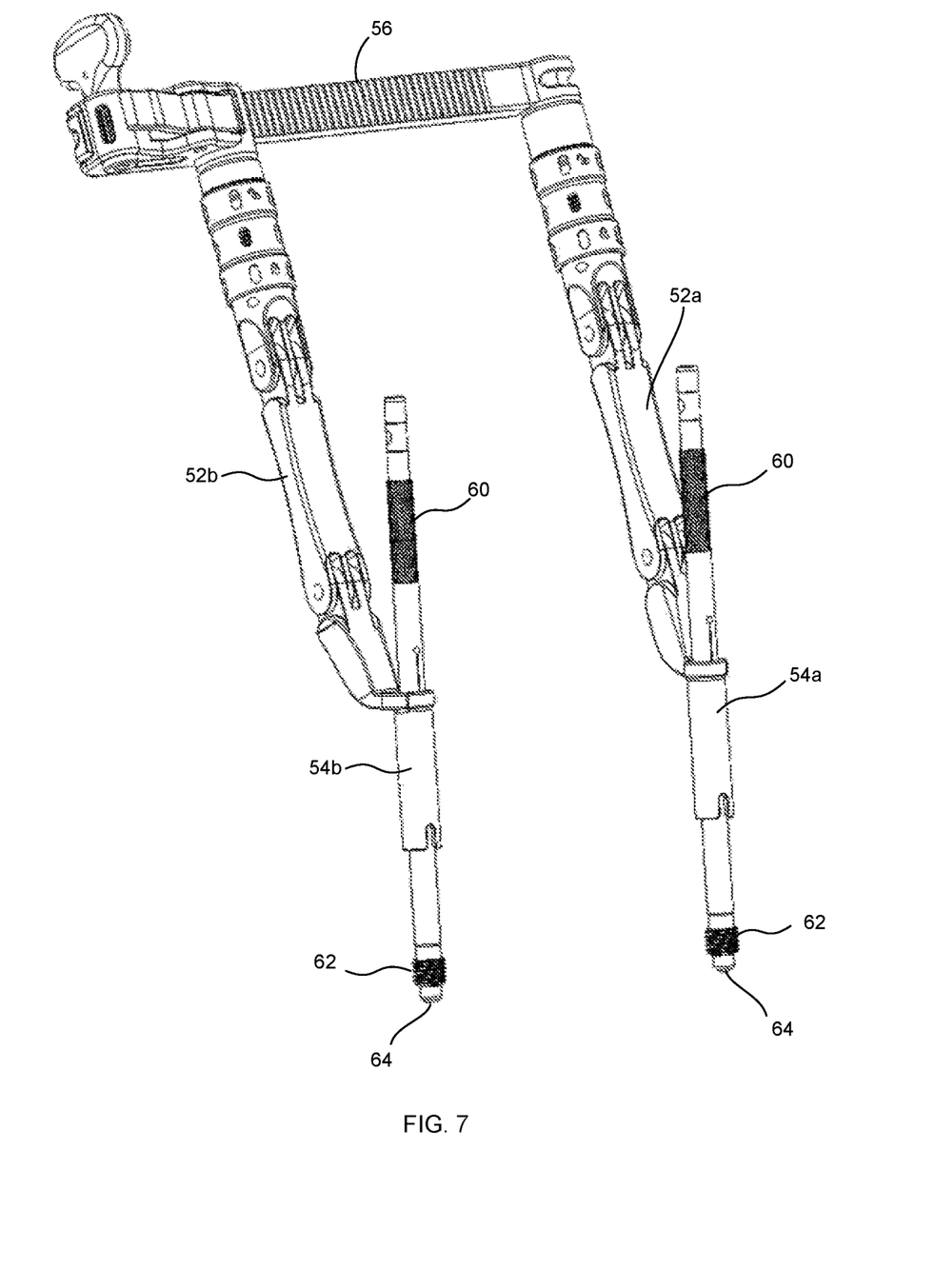
FIG. 7 illustrates the distraction instrument of FIG. 5 engaged with two distraction posts in accordance with one embodiment of the present invention.
Figure 8:
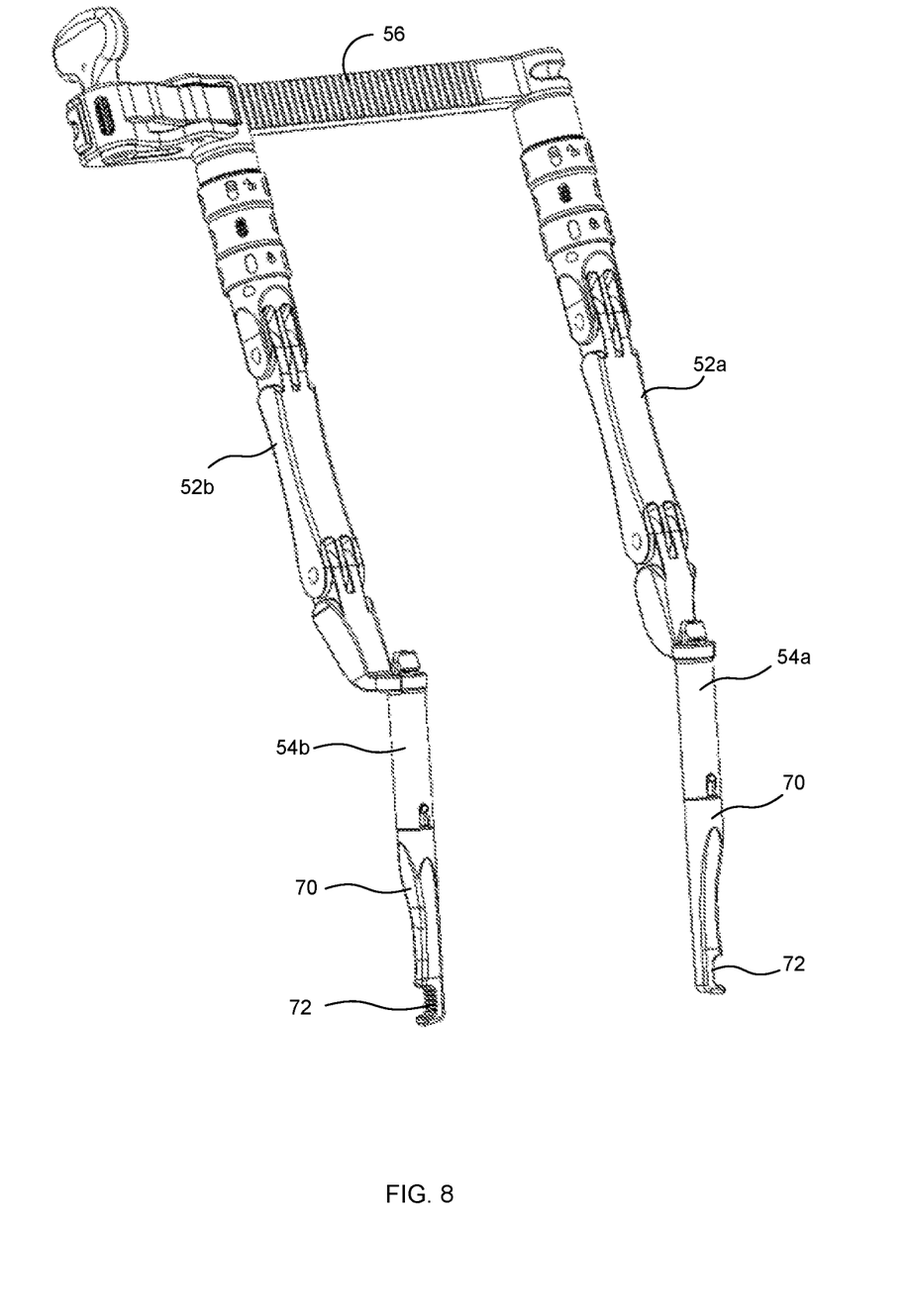
FIG. 8 illustrates the distraction instrument of FIG. 5 engaged with two lamina hooks in accordance with one embodiment of the present invention.
Figure 9:
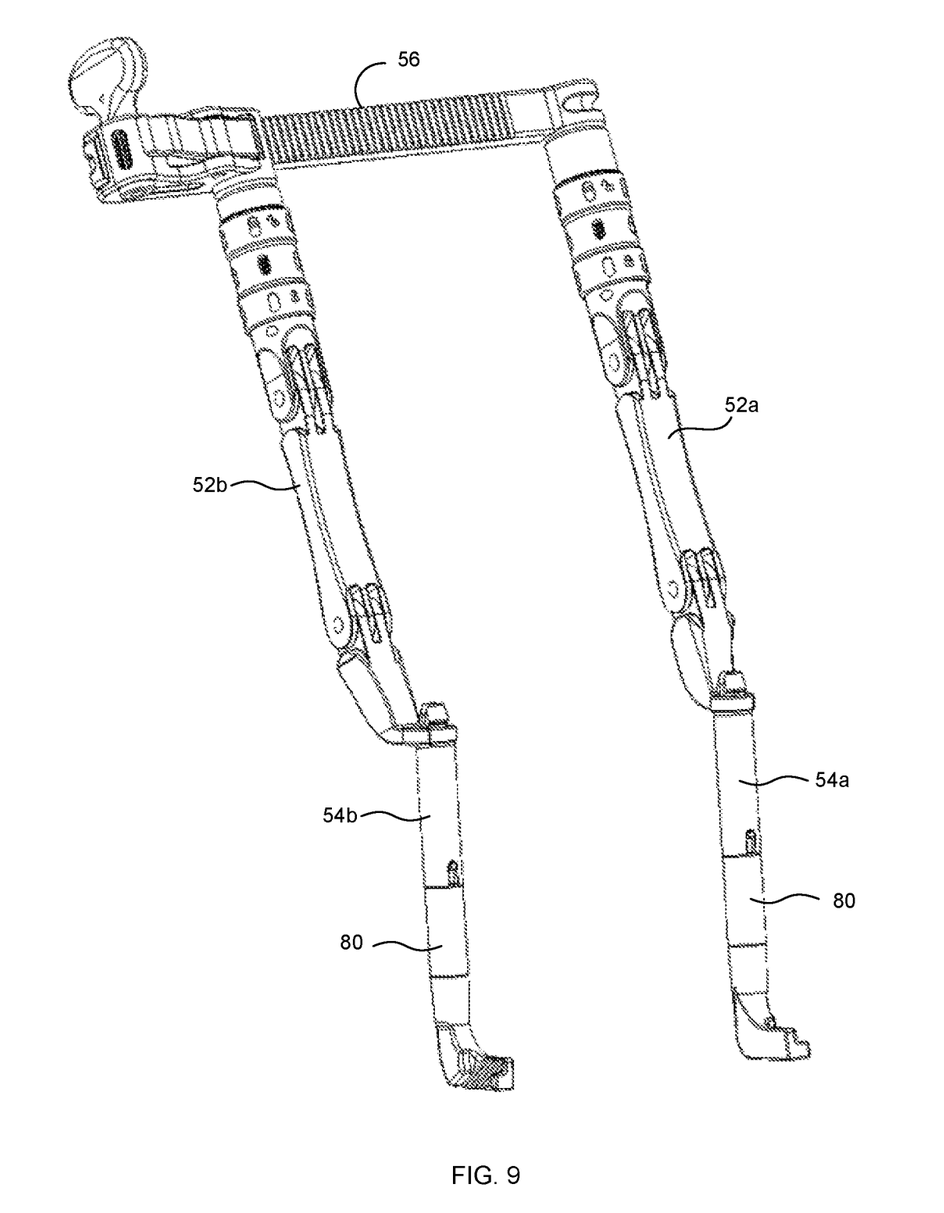
FIG. 9 illustrates the distraction instrument of FIG. 5 engaged with two spinous process hooks in accordance with one embodiment of the present invention.

FIGS. 7-9 depict other uses for distraction instrument 50. In FIG. 7, barrels 54*a* and 54*b* are shown engaged with distraction posts 60 which are designed to engage an already implanted pedicle screw and form a fixed construct. For instance, as shown, the posts include threading 62 and an engagement surface 64 on their ends that allows them to be threaded into a coupling element of a polyaxial pedicle screw. Upon the threading, surface 64 preferably engages a screw portion of the pedicle screw which results in a temporary prevention of polyaxial movement between the coupling element and screw. In other words, a fixed construct is created. Because posts 60 are sized to be received within barrels 54*a* and 54*b*, distraction instrument 50 can be utilized to compress or distraction the vertebral bodies in this situation. FIG. 8, on the other hand, depicts lamina hooks 70 engaged with the barrels. These hooks include hook portions 72 that can be utilized to engage the lamina of vertebral bodies. Thus, in this configuration, distraction instrument 50 can be utilized to compress or distract the vertebral bodies without either tap markers 10 or pedicle screws having been implanted. In FIG. 9, spinous process hooks 80 engaged with the barrels. These hooks are similar to lamina hooks 70 but are designed to engage the spinous processes to facilitate distraction or compression of the vertebral bodies.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A method of moving a vertebra comprising:
engaging a first adapter with a first member, the first member having a body and a collar extending radially outwardly from the body such that the collar and body form a monolithic structure;
after engaging the first adapter with the first member, inserting the first member into a first vertebral body at a first location so that a portion of the first adapter is captured between the collar and first vertebral body;
engaging the first adapter with an instrument after engaging the first adapter with the first member;

moving the first member by operating the instrument to move the first vertebral body;

removing the first member from the first vertebral body; and positioning a first anchor into the first vertebral body at the first location.

2. The method of claim 1, further comprising creating an opening in the vertebra prior to the inserting step and the inserting step includes inserting the first member in the opening.

3. The method of claim 2, wherein the creating an opening step comprises drilling a hole in the vertebra.

4. The method of claim 1, wherein the first member is a tap.

5. The method of claim 4, wherein the inserting step includes creating a threaded opening at the first location.

6. The method of claim 4, wherein engaging the first adapter to the first member includes passing a threaded shaft of the first member through an opening in the first adapter such that the first adapter is positioned adjacent to the collar, the collar having a cross-section dimension greater than the opening of the first adapter.

7. The method of claim 1, wherein the first anchor is a bone screw.

8. The method of claim 1, further comprising the steps of:
engaging a second adapter with a second member,
inserting the second member into a second vertebral body,
engaging the second adapter with the instrument after engaging the second adapter with the second member, and
moving the second vertebral body with respect to the first vertebral body by operating the instrument.

9. The method of claim 8, wherein the moving steps include:
moving the first and second vertebral bodies apart to distract a disc space defined by the first and second vertebral bodies, and
moving the first and second vertebral bodies together to compress the disc space.

10. The method of claim 9, further comprising the step of inserting an implant between the first and second vertebral bodies.

11. The method of claim 1, wherein the moving step includes engaging an extension portion of the first adapter with the instrument.

12. The method of claim 1, wherein:
engaging the first adapter with the first member includes inserting the first member through an opening of the first adapter so that the first member extends from opposite ends of the opening of the first adapter, and
engaging the first adapter to the instrument includes inserting an elongate shaft of the first adapter into an opening in the instrument.

13. A method of moving vertebral bodies comprising:
inserting a first tap in a first vertebral body and a second tap in a second vertebral body to create respective first and second threaded openings in the vertebral bodies, the first and second tap each having a threaded shaft, an extension portion, and a head, the extension portion having a plurality of flat surfaces positioned about an axis of the respective tap marker, the head extending from the extension and having a depression configured to engage an insertion instrument, wherein the extension portion and head have a combined axial length that is shorter than an axial length of the threaded shaft;
coupling an instrument to first and second adapters respectively engaged to the first and second taps while the taps are within the first and second threaded openings;
moving the first and second vertebral bodies with the instrument;
removing the taps;
inserting a first bone screw in the first threaded opening; and
inserting a second bone screw in the second threaded opening.

14. The method of claim 13, further comprising coupling a rod to the first and second bone screws.

15. The method of claim 13, further comprising inserting an implant between the first and second vertebral bodies.

16. The method of claim 13, wherein the moving step comprises at least one of compression and distraction of the first and second vertebral bodies.

17. The method of claim 13, wherein coupling the instrument to the first and second adapters includes inserting an elongate shaft of the first adapter into an opening in a first arm member of the instrument, and inserting an elongate shaft of the second adapter into an opening in the second arm member of the instrument, the first and second adapters remaining slidable within the respective openings of the first and second arm members once inserted therein and while the first and second vertebrae are moved by the instrument.

18. A method of compressing or distracting bone comprising:
inserting first and second taps into first and second bones to create first and second threaded openings, the first and second taps each being a monolithic structure having a threaded shaft, neck, and collar, the neck being positioned between the threaded shaft and the collar, the collar having a cross-sectional dimension larger than that of the neck;
engaging first and second adapters with the first and second taps, the first and second taps each having a shaft and a flange, the flange extending from the elongate shaft and defining an aperture extending therethrough, and wherein engaging the first and second adapters to the first and second taps includes inserting the threaded shafts of the first and second taps through the apertures of the respective first and second adapters such that the flanges of the adapters are respectively positioned about the neck and adjacent to the collar;
coupling an instrument to the shafts of the first and second adapters after engaging the first and second adapters with the first and second taps;
moving the first and second bones with the instrument while the taps are in the first and second threaded openings;
removing the taps;
inserting first and second bone screws into the first and second threaded openings; and
coupling a rod to the first and second bone screws.

19. The method of claim 18, wherein the first and second bones are first and second vertebral bodies.

* * * * *

UNITED STATES PATENT AND TRADEMARK OFFICE
CERTIFICATE OF CORRECTION

| | | |
|---|---|---|
| PATENT NO. | : 10,617,449 B2 | Page 1 of 1 |
| APPLICATION NO. | : 15/399837 | |
| DATED | : April 14, 2020 | |
| INVENTOR(S) | : Erika Corbin et al. | |

It is certified that error appears in the above-identified patent and that said Letters Patent is hereby corrected as shown below:

On the Title Page (72) Inventors:
"Nicole Renee Favetta, Haverstraw, NY (US)" should read --Nicole Renee Fallacaro, Montvale, NJ--, and
"Steven Krause" should read --Steven F. Krause--.

Signed and Sealed this
Sixteenth Day of June, 2020

Andrei Iancu
*Director of the United States Patent and Trademark Office*